United States Patent [19]

Nishimura et al.

[11] 4,346,046
[45] Aug. 24, 1982

[54] PROCESS FOR PRODUCING AMINOARYL-β-SULFATOETHYLSULFONE

[75] Inventors: Nobuzi Nishimura, Toyonaka; Utazi Sawa; Takemi Tokieda, both of Nara; Shun-ichi Hayakawa; Yasuo Tezuka, both of Ibaraki, all of Japan

[73] Assignee: Sumitomo Chemical Company, Limited, Osaka, Japan

[21] Appl. No.: 169,497

[22] Filed: Jul. 16, 1980

[30] Foreign Application Priority Data

Jul. 19, 1979 [JP] Japan .................................. 54-92201
Aug. 9, 1979 [JP] Japan .................................. 54-102075
Aug. 14, 1979 [JP] Japan .................................. 54-103656

[51] Int. Cl.$^3$ ........................................... C07C 141/16
[52] U.S. Cl. .................................................. 260/458 C
[58] Field of Search .................................... 260/458 C

[56] References Cited

U.S. PATENT DOCUMENTS

3,133,950  5/1964  Pizzarello et al. ............. 260/458 R
3,414,579 12/1968  Remy et al. .................... 260/458 C
3,900,510  8/1975  Fuchs et al. ................... 260/458 C

FOREIGN PATENT DOCUMENTS

42-16617  9/1967  Japan .............................. 260/458 C
45-27096  9/1970  Japan .............................. 260/458 C
1540565   2/1979  United Kingdom ............. 260/458 C
1540566   2/1979  United Kingdom ............. 260/458 C
1540567   2/1979  United Kingdom ............. 260/458 C

OTHER PUBLICATIONS

Gilbert, "Sulfonation and Related Reactions", Interscience Publishers, New York, 1965, pp. 347-348.

*Primary Examiner*—Nicky Chan
*Attorney, Agent, or Firm*—Stevens, Davis, Miller & Mosher

[57] ABSTRACT

An improved process for producing sulfuric acid semiesters of the formula:

$$NH_2-A(-SO_2CH_2CH_2OSO_3H)_n$$

wherein A is a substituted or unsubstituted aromatic or heterocyclic group, and n is an integer of 1 or 2, which are important as intermediate of the vinylsulfonic reactive dyes, said process comprising reacting a compound of the formula:

$$B-NH-A(-SO_2CH_2CH_2OH)_n$$

or $$CO(NH-A-SO_2CH_2CH_2OH)_2$$

wherein A and n are as defined above, and B is hydrogen or a group capable of being hydrolyzed by an acid, with an acid.

6 Claims, No Drawings

PROCESS FOR PRODUCING AMINOARYL-β-SULFATOETHYLSULFONE

This invention relates to an improved process for producing sulfuric acid semiester compounds which are important as intermediate of the vinylsulfonic reactive dyes. More particularly, the invention relates to an improved process for producing a sulfuric acid semiester of the formula (I):

$$NH_2-A+SO_2CH_2CH_2OSO_3H)_n \quad (I)$$

wherein A is a substituted or unsubstituted aromatic or heterocyclic group and, in particular, A can be phenylene, naphthylene,

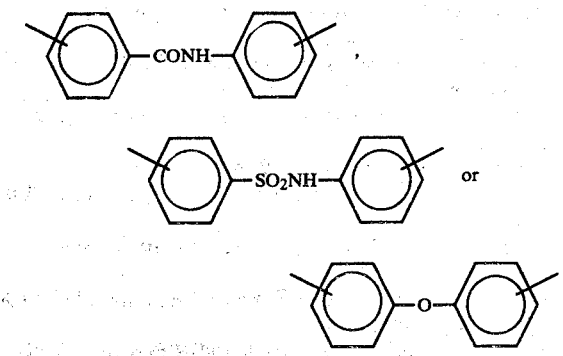

which may be substituted with one or two methyl, methoxy, hydroxy, chloro, carboxylic or sulfonic acid groups, and n is an integer of 1 or 2, which comprises reacting a compound of the formula (II) or (III):

$$B-NH-A+SO_2CH_2CH_2OH)_n \quad (II)$$

$$CO(NH-A-SO_2CH_2CH_2OH)_2 \quad (III)$$

wherein A and n are as defined above, and B is hydrogen or a group capable of being hydrolyzed by an acid, with an acid.

The prior art methods for converting, for example, a compound of the formula (II) into a compound of formula (I) required the troublesome operations and also necessitated use of a large excess of sulfuric acid for obtaining the objective compound in a high yield. More specifically, aminoaryl-β-sulfatoethylsulfone for instance has been produced by hydrolyzing acetylaminoaryl-β-hydroxyethylsulfone in hydrochloric acid or dilute sulfuric acid to obtain aminoaryl-β-hydroxyethylsulfone and then, after isolating and drying, esterifying it in concentrated sulfuric acid. According to this method, however, the isolation yield of aminoaryl-β-hydroxyethylsulfone is low and also the operation is complicated as isolating and drying are required, so that this method is of little use in industrial applications.

Published Examined Japanese Patent Application No. 16617/1967 disclosed a method in which 4-acetylaminophenyl-β-hydroxyethylsulfone is hydrolyzed and simultaneously esterified by using concentrated sulfuric acid or a mixture of concentrated sulfuric acid and an organic solvent. In this method, however, as described in its Examples, in order to hydrolyze 4-acetylaminophenyl-β-hydroxyethylsulfone and convert resulting 4-aminophenyl-β-hydroxyethylsulfone and 4-aminophenyl-β-acetoxyethylsulfone into 4-aminophenyl-β-sulfatoethylsulfone, it is necessary to add a large quantity of fuming sulfuric acid in the reaction solution. For example, the amount of sulfuric acid used is as much as 8.4 to 15.6 moles per mole of the starting material acetylaminophenyl-β-hydroxyethylsulfone. Accordingly, the product 4-aminophenyl-β-sulfatoethylenesulfone is obtained in the form of a large volume of concentrated sulfuric acid solution or fuming sulfuric acid solution, so that it is necessary to treat a large quantity of acid no matter whether the product is put to use as is or isolated by means of dilution. Thus, this method involves the problem of cost of the alkali agent required for the treatment of excess sulfuric acid and the problem of separation of the resultant sulfuric acid salt and hence is unfit for the industrial applications.

Published Examined Japanese Patent Application No. 27096/1970 shows a method of producing aminoaryl-β-sulfatoethylsulfone by hydrolyzing acetylaminoaryl-β-sulfatoethylsulfone with use of sulfuric acid having a concentration of 50% or less at 45° C. This method, however, has the drawbacks that a long time is required for the reaction and that the product yield is lowered because hydrolysis of the sulfuric ester in the β-sulfatoethylsulfonyl group takes place concurrently with hydrolysis of the acetylamino group. Moreover, even in this method which can be said to be a typical case using a relatively small amount of sulfuric acid, use of as many as 4.9 moles of sulfuric acid is required.

For the purpose of solving these problems, West German Patent Laid-Open No. 1,443,877 proposed a method of producing sulfuric acid semiester compounds in a water-soluble organic solvent such as pyridine or picoline using amidosulfonic acid in an amount of 3 to 4 moles. This method is valued in that it is capable of reducing the esterifying agent which had been used in excess in conventional methods, but this method still has the problem that the water-soluble organic solvent used must be later distilled off sufficiently under reduced pressure. Further, inspite of such distillation treatment, there still remains approximately ¼ of the used water-soluble organic solvent in the sulfuric acid semiester, so that recovery or removal of such solvent in some way or other, before the waste solution reaches the drain, is required. Another defect of this method is that, as it is difficult to bring a water-soluble organic solvent into a perfectly water-free state, the reaction temperature is relatively high and hence hydrolysis of amidosulfonic acid tends to take place. Thus, the hydrolyzed amidosulfonic acid must be supplemented, resulting in use of a considerable amount of excess esterifying agent.

As a result of extensive studies for eliminating said disadvantages of the heretofore known methods, the present inventors succeeded in obtaining an improved process for producing a high-purity sulfuric acid semiester compound in a substantially quantitative yield and in an industrially advantageous way by using a substantially theoretical amount of an acid and without producing any waste solution which might cause environmental pollution, by reacting a compound of said formula (II) or (III) with an acid in a specific pattern of reaction.

Thus, the present invention provides a process for producing a sulfuric acid semiester of the formula (I):

$$NH_2-A-SO_2CH_2CH_2OSO_3H)_n \quad (I)$$

wherein A is a substituted or unsubstituted aromatic or heterocyclic group and, in particular, A can be phenylene, naphthylene,

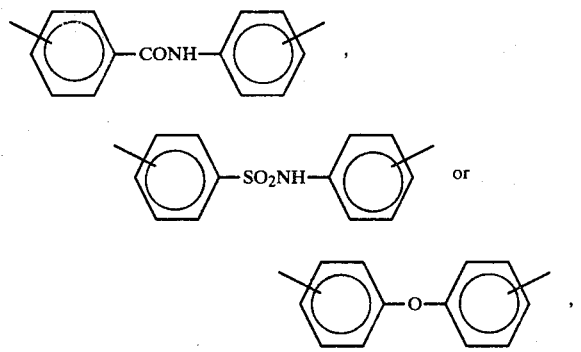

which may be substituted with one or two methyl, methoxy, hydroxy, chloro, carboxylic or sulfonic acid groups, and n is an integer of 1 or 2, which comprises subjecting a mixture of an acid and a compound of the formula (II) or (III):

$$B-NH-A-SO_2CH_2CH_2OH)_n \qquad (II)$$

$$CO(NH-A-SO_2CH_2CH_2OH)_2 \qquad (III)$$

wherein A and n are as defined above, and B is hydrogen or a group capable of being hydrolyzed by an acid, to reaction while removing a volatile matter from the reaction system, in a reaction zone capable of (1) removing the volatile matter by azeotropy with an organic solvent, evaporation or vaporization, using as the acid sulfuric acid and/or sulfamic acid, or (2) kneading the mixture, using as the acid sulfuric acid, sulfamic acid, chlorosulfonic acid or a mixture of sulfuric acid with sulfamic acid, chlorosulfonic acid or sulfur trioxide.

The present invention is described in further detail hereinbelow.

The compounds of formula (II) include the following:

4-(amino or acetylamino)phenyl-β-hydroxyethylsulfone,
2-methoxy-5-(amino or acetylamino)phenyl-β-hydroxyethylsulfone,
2-methyl-4-(amino or acetylamino)-5-methoxyphenyl-β-hydroxyethylsulfone,
3-(amino or acetylamino)-4-methoxyphenyl-β-hydroxyethylsulfone,
3-(amino or acetylamino)phenyl-β-hydroxyethylsulfone,
4-(amino or acetylamino)-2,5-dimethoxyphenyl-β-hydroxyethylsulfone,
5-(amino or acetylamino)-2,4-dimethoxyphenyl-β-hydroxyethylsulfone,
3-chloro-4-(amino or acetylamino)-phenyl-β-hydroxyethylsulfone,
3-(amino or acetylamino)-4-chlorophenyl-β-hydroxyethylsulfone,
2-methyl-5-(amino or acetylamino)phenyl-β-hydroxyethylsulfone,
3-carboxy-4-(amino or acetylamino)phenyl-β-hydroxyethylsulfone,
3-hydroxy-4-(amino or acetylamino)phenyl-β-hydroxyethylsulfone,
3-amino-4-sulfophenyl-β-hydroxyethylsulfone,
2-(amino or acetylamino)phenyl-β-hydroxyethylsulfone,
5-(amino or acetylamino)-1-naphthyl-β-hydroxyethylsulfone,
4-(amino or acetylamino)-1-naphthyl-β-hydroxyethylsulfone,
5-(amino or acetylamino)-2-naphthyl-β-hydroxyethylsulfone,
7-(amino or acetylamino)-1-naphthyl-β-hydroxyethylsulfone,
2-(amino or acetylamino)-6-(β-hydroxyethylsulfonyl)-1-naphthalenesulfonic acid,
3-(3- or 4-aminobenzoyl)aminophenyl-β-hydroxyethylsulfone,
3-(3- or 4-aminobenzoyl)amino-4-methoxyphenyl-β-hydroxyethylsulfone,
3-(4-acetylaminophenylsulfonyl)aminophenyl-β-hydroxyethylsulfone,
3-(4-aminophenylsulfonyl)aminophenyl-β-hydroxyethylsulfone,
4-(4-acetylaminophenoxy)phenyl-β-hydroxyethylsulfone,
4-(4-aminophenoxy)phenyl-β-hydroxyethylsulfone,
4-(ureido or benzoylamino)phenyl-β-hydroxyethylsulfone,
2-methoxy-5-(ureido or benzoylamino)phenyl-β-hydroxyethylsulfone,
3-(ureido or benzoylamino)-4-methoxyphenyl-β-hydroxyethylsulfone,
3-(ureido or benzoylamino)phenyl-β-hydroxyethylsulfone,
2-methyl-4-(ureido or benzoylamino)-5-methoxyphenyl-β-hydroxyethylsulfone,
4-(ureido or benzoylamino)-2,5-dimethoxyphenyl-β-hydroxyethylsulfone,
3-chloro-4-(ureido or benzoylamino)-phenyl-β-hydroxyethylsulfone,
2-methyl-5-(ureido or benzoylamino)phenyl-β-hydroxyethylsulfone,
3-(ureido or benzoylamino)-4-sulfophenyl-β-hydroxyethylsulfone,
2-(ureido or benzoylamino)phenyl-β-hydroxyethylsulfone,
5-(ureido or benzoylamino)-1-naphthyl-β-hydroxyethylsulfone,
4-(ureido or benzoylamino)-1-naphthyl-β-hydroxyethylsulfone,
4-(ureido or benzoylamino)-2-napthyl-β-hydroxyethylsulfone,
5-(ureido or benzoylamino)-2-naphthyl-β-hydroxyethylsulfone,
7-(ureido or benzoylamino)-1-naphthyl-β-hydroxyethylsulfone, and
2-(ureido or benzoylamino)-6-(β-hydroxyethylsulfonyl)-1-naphthalenesulfonic acid.

The compounds of the formula (III) include the following:
N,N'-bis[m-, or p-(β-hydroxyethylsulfonyl)phenyl]urea,
N,N'-bis[4-methoxy-3-(β-hydroxyethylsulfonyl)phenyl]urea,
N,N'-bis[2-methoxy-5-(β-hydroxyethylsulfonyl)phenyl]urea,
N,N'-bis[2-methoxy-5-methyl-4-(β-hydroxyethylsulfonyl)phenyl]urea,
N,N'-bis[2-sulfo-5-(β-hydroxyethylsulfonyl)phenyl]urea, N,N'-bis[4-(β-hydroxyethylsulfonyl)-1-naphthyl]urea,
N,N'-bis[6-(β-hydroxyethylsulfonyl)-1-naphthyl]urea,
N,N'-bis[8-(β-hydroxyethylsulfonyl)-2-naphthyl]urea, and
N,N'-bis[1-sulfo-6-(β-hydroxyethylsulfonyl)-2-naphthyl]urea These compounds can be used even in a hydrous state. This makes it possible to avoid the troublesome operations such as drying and pulverization, making the method of this invention more advantageous than the conventional methods.

The acids usable in this invention include sulfuric acid, sulfamic acid, chlorosulfonic acid and mixtures of sulfuric acid with sulfamic acid, chlorosulfonic acid or sulfur trioxide. Among them, sulfuric acid is most preferred from the industrial view point. In some cases where a certain specified type of compounds is used as a starting material, a mixture of sulfuric acid and sulfamic acid allows advantageous advancement of the reaction and proves desirable in respect of the material of the reaction apparatus.

The amount of the acid used in this invention is within the range of 1 to 3 moles, preferably 1 to 2 moles, for one β-hydroxyethylsulfonyl group in the compound of the formula (II) or (III). In case of using a mixture of sulfuric acid and sulfamic acid or chlorosulfonic acid, the mixing molar ratio of sulfamic acid or chlorosulfonic acid to sulfuric acid is 0.1–3.0, preferably 0.1–2.0.

In case of using sulfuric acid in the reaction of this invention, the initial concentration of sulfuric acid in the reaction system $H_2SO_4/(H_2SO_4+H_2O)$, although not limited to any specific range, is usually 20 to 100 wt%, preferably 40 to 98 wt%. In case the compound of the formula (II) or (III) is in a hydrous state, the concentration of sulfuric acid used is properly selected according to the degree of the hydrous state, and in some cases, fuming sulfuric acid is used.

The reaction temperature is suitably decided depending on the properties of the starting compound, the pattern of reaction and the reaction apparatus employed, but usually it is between 40° C. and 250° C. However, in case of performing the reaction azeotropically with an organic solvent, the reaction temperature is preferably 50° to 200° C., more preferably 70° to 180° C., and in case of carrying out the reaction by means of kneading, the reaction temperature is preferably 50° to 180° C., more preferably 50° to 140° C. When the reaction is carried out by means of evaporation or vaporization, the reaction temperature is preferably 50° to 250° C., more preferably 80° to 200° C. The higher the temperature, the more facilitated is the progress of the reaction, but too high temperature tends to invite a side reaction to adversely affect the objective product. In case of employing an apparatus capable of shortening reaction time, a relatively high temperature can be used.

The organic solvents usable when performing the reaction azeotropically therewith are those which are inert to said acids and have the ability to form an azeotrope with water or water and volatile matter at 50°–200° C. Examples of such organic solvents include cyclohexane, heptane, benzene, toluene, xylene, solvent naphtha, trichloroethane, dichloropropane, trichloroethylene, tetrachloroethane, perchloroethylene, chlorobenzene, dichlorobenzene, nitrobenzene and methyl isobutyl ketone. Such organic solvents are in an amount of 0.1 to 10 times, preferably 0.1 to 8 times the weight of the starting compound of the formula (II) or (III).

In case of carrying out the reaction by means of kneading, there is preferably employed an apparatus which has a batchwise or continuous stirring or grinding capacity generally used for mixing the viscous or tacky materials. Examples of the batchwise apparatus usable in this invention are ribbon mixer, pug mill and double-arm kneader (for example, dispersion kneader), and examples of the continuous apparatus are continuous kneader and auger extruder.

For performing the reaction by means of evaporation or vaporization, there can be favorably used a batchwise or continuous evaporator, concentrator or dryer, and examples of such apparatus are tray dryer, spray dryer, airborne dryer, rotary dryer, tunnel and band dryer, drum dryer, cylinder dryer, continuous ventilation dryer, infrared dryer, high-frequency dryer, pipe reactor, stirring evaporator and rotary concentrator.

When the reaction of this invention is carried out by said kneading means or evaporating or vaporizing means, the above-said type of organic solvents may be used for facilitating the reaction.

In the present invention, the volatile matter to be removed from the reaction system is variable depending on the type of the starting compound (II) or (III) and the acid used, and includes water and other by-produced matters such as acetic acid, hydrogen chloride, ammonia, carbon dioxide gas, etc. It can be removed from the reaction system either azeotropically with the aforesaid organic solvent, or by evaporation or vaporization, or by means of absorption (for example, of water into sulfur dioxide) for conversion (for example, of ammonia into its salt). For facilitating such removal, an inert gas such as nitrogen gas, air or carbon dioxide gas may be blown into the reaction solution or the operation may be performed under reduced pressure, and in order to improve heat transfer, an inert material such as diatomaceous earth, activated clay, active carbon, silica gel, brown coal, etc., may be used. It is also possible to add aminoaryl-β-sulfatoethylsulfone corresponding to the reaction product. The reaction mixture comprising the desired sulfuric acid semiester obtained according to the process of this invention itself or a dilute solution obtainable by pouring the reaction mixture into water and then neutralizing with alkali agent such as sodium hydroxide, sodium carbonate, sodium hydrogen carbonate or potassium carbonate etc., may be immediately used as intermediate for reactive dyes. The reaction mixture obtained according to the process of this invention using organic solvent and/or inert material such as diatomaceous earth, activated clay, etc., is poured into water and then neutralized with an alkali agent as described above. After the organic solvent and/or the inert material are removed by filtration, decantation or the like, the obtained dilute solution in water of the alkali metal salt of the sulfuric acid semiester may be used as intermediate for reactive dyes.

Now, the process of this invention is described in further detail by way of the examples thereof, but the invention is not limited to these examples. All "parts" and "%" in the following examples are by weight unless otherwise specified.

EXAMPLE 1

49.5 Parts of 4-acetylaminophenyl-β-hydroxyethylsulfone (purity: 98.2%) was added in 29.4 parts of 70% sulfuric acid (molar ratio: 1.05) under stirring and the mixture was maintained at 100°–105° C. for one hour. The obtained mixture was poured into 200 parts of perchloroethylene of 115°–120° C. for a period of 2 hours while distilling off acetic acid and water, and then the mixture was maintained at 115°–120° C. for additional one hour to complete the reaction.

A liquid chromatograph of the obtained reaction product showed 97% yield of 4-aminophenyl-β-sulfatoethylsulfone and containment of small quantities of 4-aminophenyl-β-hydroxyethylsulfone and 4-aminophenyl-β-acetoxyethylsulfone in the product.

EXAMPLE 2

40 Parts of diatomaceous earth, 49.5 parts of 4-acetylaminophenyl-β-hydroxyethylsulfone (purity: 98.2%) and 21.7 parts of 95% sulfuric acid (molar ratio: 1.05) were added in 300 parts of o-dichlorobenzene and reacted under reduced pressure (200 mmHg) at 100°–105° C. for 8 hours while distilling off water and acetic acid. There was obtained 4-aminophenyl-β-sulfatoethylsulfone in a yield of 95%.

EXAMPLE 3

The process of Example 2 was followed under normal pressure by blowing nitrogen gas at 100°–105° C. for 8 hours. A liquid chromatograph of the reaction product showed 95% yield of the objective material same as in Example 2.

EXAMPLE 4

57.5 Parts of 2-methoxy-5-acetylaminophenyl-β-hydroxyethylsulfone (purity: 95%) was added in 39.2 parts of 65% sulfuric acid (molar ratio: 1.3) under stirring and maintained at 100°–105° C. for 2 hours. The obtained mixture was poured into 150 parts of toluene added with 40 parts of diatomaceous earth and maintained at 105°–110° C., while distilling off water and acetic acid for a period of 2 hours. Then the mixture was maintained at 105°–110° C. for one hour to complete the reaction. A liquid chromatograph of the reaction product showed 95% yield of 2-methoxy-5-aminophenyl-β-sulfatoethylsulfone.

EXAMPLE 5

56.3 Parts of 3-acetylamino-4-methoxyphenyl-β-hydroxyethylsulfone (purity: 97%) was added in 39.2 parts of 60% sulfuric acid (molar ratio: 1.2) under stirring and maintained at 100°–105° C. for 2 hours. Then the mixture was poured under reduced pressure (400 mmHg) into 200 parts of o-dichlorobenzene, which had been added with 10 parts of 3-amino-4-methoxyphenyl-β-sulfatoethylsulfone and maintained at 90°–95° C., while distilling off acetic acid and water for a period of 2 hours, and the mixture was maintained at 90°–95° C. for an additional 2 hours to complete the reaction. Analysis of the reaction product by liquid chromatography showed 90% yield of 3-amino-4-methoxyphenyl-β-sulfatoethylsulfone.

EXAMPLE 6

40 Parts of diatomaceous earth, 50.3 parts of wet cake of 3-aminophenyl-β-hydroxyethylsulfone (purity: 80%) and 24.8 parts of 95% sulfuric acid (molar ratio: 1.2) were added in 300 parts of o-dichlorobenzene under stirring and reacted at 160°–165° C. for 5 hours while distilling off water. There was obtained 3-aminophenyl-β-sulfatoethylsulfone in a yield of 97%.

EXAMPLES 7–15

The compounds shown in column 2 of Table 1 were reacted in the same way as Example 1 in the organic solvents shown in column 3 by using sulfuric acid in amounts shown in column 4 and adding diatomaceous earth in amounts shown in column 5 at the reaction temperatures shown in column 6 to obtain the objective sulfuric acid semiester compounds in the yields shown in column 7. The yield was measured by liquid chromatography.

TABLE 1

| No. | Compound | Kind and amount of organic solvent | Concent., amount and mol ratio of sulfuric acid used | Amount of diatom. earth | Reaction temperature | Yield |
|---|---|---|---|---|---|---|
| 7 | 2-methyl-4-acetylamino-5-methoxyphenyl-β-hydroxyethylsulfone | Xylene 120 (parts) | 50%, 42.2 parts, 1.05 | 0 (part) | 105–110° C. | 95% |
| 8 | 3-(4-aminobenzoyl)-aminophenyl-β-hydroxyethylsulfone | Toluene 200 (parts) | 98%, 21 parts, 1.05 | 40 (parts) | 105–120° C. | 95% |
| 9 | 4-acetylaminophenyl-β-hydroxyethylsulfone | Methyl iso-butyl ketone 200 (parts) | 70%, 28 parts, 1.0 | 20 (parts) | 105–110° C. | 85% |
| 10 | 4-acetylaminophenyl-β-hydroxyethylsulfone | Toluene 200 (parts) | 70%, 28 parts, 1.0 | 15 (parts) | " | 93% |
| 11 | 4-acetylaminophenyl-β-hydroxyethylsulfone | Xylene 200 parts | 70%, 28 parts, 1.0 | 0 | 120–125° C. | 93% |
| 12 | 4-acetylaminophenyl-β-hydroxyethylsulfone | Toluene 200 parts | 70%, 30.8 parts, 1.1 | " | 105–110° C. | 96% |
| 13 | 4-acetylaminophenyl-β-hydroxyethylsulfone | Perchloroethylene 200 parts | 70%, 42.0 parts, 1.5 | " | 115–120° C. | 94% |
| 14 | 4-acetylaminophenyl-β-hydroxyethylsulfone | Perchloroethylene 200 parts | 70%, 56 parts, 2.0 | 20 | " | 93% |
| 15 | 4-acetylaminophenyl-β-hydroxyethylsulfone | Nitrobenzene 200 parts | 70%, 84 parts, 3.0 | 50 | 170–175° C. | 81% |
| 16 | N,N'-bis[p-(β-hydroxyethylsulfonyl)phenyl] urea | Chlorobenzene 300 parts | 60%, 49 parts, 1.5 | 50 | 120–128° C. | 93% |

EXAMPLE 17

72.2 Parts of wet cake of 3-acetylamino-4-methoxyphenyl-β-hydroxyethylsulfone (purity: 75.6%) was added in 23.3 parts of 5% fuming sulfuric acid (molar ratio: 1.2) under stirring while cooling to 20°–30° C., and then the mixture was maintained at 100°–105° C. for 2 hours. This mixture was poured into 200 parts of o-dichlorobenzene (which had been added with 40 parts of diatomaceous earth and maintained at 100°–105° C.) under reduced pressure (500 mmHg) for a period of 2 hours while distilling off acetic acid and water, and the mixture was maintained at 100°–105° C. for additional 2 hours to complete the reaction. A liquid chromatograph of the reaction product showed 90% yield of 3-amino-4-methoxyphenyl-β-sulfatoethylsulfone.

EXAMPLE 18

266.5 Parts of 7-amino-1-naphthyl-β-hydroxyethylsulfone (purity: 95%), 120 parts of 98% sulfuric acid (molar ratio: 1.2) and 133 parts of o-dichlorobenzene were fed into a double-arm kneader (manufactured by Moriyama Seisakujo Co.) operated at 80/60 r.p.m., and the mixture was maintained at 100°–105° C. under reduced pressure (150 mmHg) for 5 hours while distilling off produced water to complete the reaction. The obtained reaction product was analyzed by liquid chromatography, obtaining 7-amino-1-naphthyl-β-sulfatoethylsulfone in a yield of 93%.

EXAMPLE 19

247.5 Parts of 4-acetylaminophenyl-β-hydroxyethylsulfone (purity: 98.2%) and 105 parts of 98% sulfuric acid (1.05 times in molar quantity) were fed into a commercial two-shaft double-arm kneader (Inoue Seisakujo Co.) having a heating or cooling jacket and operated at 60/45 r.p.m., and the mixture was maintained at 100°–105° C. under reduced pressure (400 mmHg) for 6 hours while distilling off water and acetic acid. Liquid chromatography of the reaction product showed 96% yield of 4-aminophenyl-β-sulfatoethylsulfone. It was also found that there were contained small quantities of 4-aminophenyl-β-hydroxyethylsulfone and 4-aminophenyl-β-acetoxyethylsulfone.

EXAMPLE 20

281.6 Parts of 2-methoxy-5-acetylaminophenyl-β-hydroxyethylsulfone (purity: 97%) was added in 165.8 parts of 65% sulfuric acid (1.1 time in molar quantity) under stirring, and the mixture was maintained at 100°–105° C. for 2 hours. Then this mixture was poured into a ribbon mixer (manufactured by Moriyama Seisakujo Co.) operated at 70 r.p.m. and having already contained therein 500 parts of a diatomaceous earth, said pouring being effected for a period of 20 minutes. The mixture was maintained at 102°–125° C. for 7 hours while distilling off acetic acid and water. A liquid chromatograph of the reaction product showed 94% yield of 2-methoxy-5-aminophenyl-β-sulfatoethylsulfone.

EXAMPLE 21

281.5 Parts of 3-acetylamino-4-methoxyphenyl-β-hydroxyethylsulfone (purity: 97%) and 134.1 parts of 95% sulfuric acid (1.3 times in molar quantity) were supplied into a pug mill (Kurimoto Iron Works) operated at 80 r.p.m., and the mixture was maintained at 100°–105° C. under reduced pressure (500 mmHg) for 4 hours while distilling off water and acetic acid.

Analysis of the reaction mixture by liquid chromatography gave 94% yield of 3-amino-4-methoxyphenyl-β-sulfatoethylsulfone.

EXAMPLE 22

247.5 Parts of 4-acetylaminophenyl-β-hydroxyethylsulfone (purity: 98.2%) and 300 parts of diatomaceous earth were fed into a two-shaft double-arm kneader (Inoue Seisakujo Co.) operated at 60/45 r.p.m., followed by pouring thereinto of 105 parts of 98% sulfuric acid (molar ratio: 1.05). Then 250 parts of xylene was added dropwise under reduced pressure (500 mmHg), and the mixture were maintained at 120°–125° C. for 6 hours while distilling off acetic acid and water to complete the reaction. A liquid chromatograph of the reaction product showed production of 4-amino-β-sulfatoethylsulfone in a yield of 95%.

EXAMPLE 23

304.5 Parts of 3-aminophenyl-β-hydroxyethylsulfone (purity: 66%) was fed, in the form of a wet cake, into a two-shaft double-arm kneader (Inoue Seisakujo Co.) having a heating-cooling jacket and operated at 60/45 r.p.m., and water was distilled off under reduced pressure (600 mmHg) at 100°–105° C. At a point when distilling-off of water was no longer noticed, pressure reduction was released and the mixture was cooled to 50° C., added with 120 parts of 65% fuming sulfuric acid (molar ratio: 1.4) and maintained at 50°–60° C. for 3 hours. Production of 3-aminophenyl-β-sulfatoethylsulfone in a yield of 92% was ascertained as a result of liquid chromatographic analysis of the reaction product.

EXAMPLE 24

450.5 Parts of N,N'-bis[4-(β-hydroxyethylsulfonyl)-phenyl]urea (purity: 95%) and 228.7 parts of 60% sulfuric acid (molar ratio: 0.7) were added into a dispersion kneader (manufactured by Moriyama Seisakujo Co.) operated at 70 r.p.m. and maintained at 100°–105° C. for 3 hours, and then water was distilled off under reduced pressure (500 mmHg). When distilling-off of water has ended, the mixture was cooled to 50° C., added with 170 parts of 28% fuming sulfuric acid (molar ratio: 0.9) and maintained at 50°–60° C. Liquid chromatograph of the reaction product showed 90% yield of 4-aminophenyl-β-sulfatoethylsulfone.

EXAMPLES 25–34

The reaction process of Example 19 was repeated but by changing the starting material, type of reactor, its operating speed, sulfuric acid concentration, amount of sulfuric acid added and degree of pressure reduction as shown in the following table 2. The objective products were obtained in the yields also shown in the following table 2.

TABLE 2

| Example No. | Starting material | Reactor | Operating speed rpm | Sulfuric acid concentration (%) | Amount of sulfuric acid (molar ratio) | Pressure (mmHg) | Reaction temperature (°C.) | Yield (%) |
|---|---|---|---|---|---|---|---|---|
| 25 | 4-Amino-2,5-dimethoxyphenyl-β-hydroxyethylsulfone | Two-shaft double-arm kneader | 60/45 | 100 | 1.7 | 100 | 80–85 | 92 |
| 26 | 3-Chloro-4-aminophenyl-β-hydroxyethylsulfone | Two-shaft double-arm kneader | " | 98 | 1.1 | Normal pressure | 120–125 | 92 |
| 27 | 3-Amino-4-sulfophenyl-β-hydroxyethylsulfone | Two-shaft double-arm kneader | " | 95 | 2.0 | 500 | 100–105 | 94 |
| 28 | 4-Amino-1-naphthyl-β-hydroxyethylsulfone | Two-shaft double-arm kneader | " | 90 | 1.2 | Normal pressure | 115–120 | 93 |
| 29 | 3-(4-Aminobenzoyl)aminophenyl-β-hydroxyethylsulfone | Two-shaft double-arm kneader | " | 100 | 1.05 | 500 | 100–105 | 95 |
| 30 | 2-Methyl-4-acetylamino-5-methoxyphenyl-β-hydroxyethylsulfone | Dispersion kneader | 70 | 70 | 1.5 | 100 | 80–85 | 94 |
| 31 | 3-Aminophenyl-β-hydroxyethylsulfone | Double-arm kneader | 80/60 | 100 | 1.05 | Normal pressure | 130–135 | 96 |
| 32 | 7-Amino-1-naphthyl-β-hydroxyethylsulfone | Two-shaft double-arm kneader | 60/45 | 98 | 1.2 | 500 | 95 | 94 |
| 33 | N,N'-bis[3-(β-hydroxyethylsulfonyl)-4-methoxyphenyl]-urea | Two-shaft double-arm kneader | 40 | 70 | 1.05 | " | 105 | 92 |
| 34 | 4-Acetylaminophenyl-β-hydroxyethylsulfone | Kurimoto continuous kneader | 20 | " | " | Normal pressure | 120–125 | 94 |

EXAMPLE 35

49.5 Parts of 4-acetylaminophenyl-β-hydroxyethylsulfone (purity: 98.2%) was added into 29.4 parts of 70% sulfuric acid (1.05 times in molar quantity) and maintained at 50°–60° C. for 2 hours. The obtained mixture was placed in an evaporating dish and kept in a hot air circulation dryer (manufactured by Nishiyama Seisakujo Co.) at 110°–115° C. for 8 hours. Water and acetic acid were distilled off during this period. A liquid chromatograph of the resultant reaction product showed formation of 4-aminophenyl-β-sulfatoethylsulfone in a yield of 98.5% and contained small quantities of 4-aminophenyl-β-hydroxyethylsulfone and 4-aminophenyl-β-acetoxyethylsulfone in the product.

EXAMPLE 36

56.3 Parts of 2-methoxy-5-acetylaminophenyl-β-hydroxyethylsulfone (purity: 97%) was added in 33.2 parts of 65% sulfuric acid (1.1 time in molar quantity) under stirring and the mixture was maintained at 100°–105° C. for 2 hours. This mixture was mixed well with 40 parts of diatomaceous earth and maintained at 80°–85° C. for 6 hours by using a rotary vacuum evaporator (manufactured by Tokyo Physical and Chemical Instruments Co.) while distilling off water and acetic acid. A liquid chromatograph of the reaction product showed 97% yield of 2-methoxy-5-aminophenyl-β-sulfatoethylsulfone.

EXAMPLE 37

281.5 Parts of 3-acetylamino-4-methoxyphenyl-β-hydroxyethylsulfone (purity: 97%) was added in 196 parts of 60% sulfuric acid (1.2 times in molar quantity) under stirring and maintained at 100°–105° C. for 2 hours, and the mixture was then spray-dried by using a spray dryer with inlet temperature of 200° C. and outlet temperature of 110°–120° C., whereby the volatile matters, that is, water and acetic acid were removed and a powdery reaction product was obtained. A liquid chromatograph of this reaction product revealed 95% yield of 3-amino-4-methoxyphenyl-β-sulfatoethylsulfone.

EXAMPLE 38

292.9 Parts of 2-methyl-4-acetylamino-5-methoxyphenyl-β-hydroxyethylsulfone (purity: 98%) was added in 140 parts of 70% sulfuric acid (1.0 time in molar quantity) and maintained at 100°–105° C. for 2 hours. The obtained mixture was continuously spread thinly on a 10 cm wide Teflon plate moving at a rate of 30 cm/min and passed in an aerated vessel kept at a temperature of 100°–105° C. Water and acetic acid were removed continuously during this period.

The flake-like reaction product produced continuously from the vessel outlet was analyzed by liquid chromatography, whereby production of 2-methyl-4-amino-5-methoxyphenyl-β-sulfatoethylsulfone in a yield of 95% was determined.

EXAMPLE 39

29.4 Parts of 100% sulfuric acid (1.5 times in molar quantity), 41.9 parts of 3-aminophenyl-β-hydroxyethylsulfone (purity: 96%) and 40 parts of diatomaceous earth were mixed well and this mixture was kept at 120°–125° C. in a hot air circulation dryer (manufactured by Yasuda Precision Machinery Co.) for 8 hours. A liquid chromatograph of the resultant reaction product showed 95% yield of 3-aminophenyl-β-sulfatoethylsulfone.

EXAMPLE 40

62.1 Parts of 7-acetylamino-1-naphthyl-β-hydroxyethylsulfone (purity: 95%) was added in 65.3 parts of 60% sulfuric acid under stirring and maintained at 100°–105° C. for 2 hours. The mixture was then placed in an evaporating dish and kept at 90°–95° C. in a vacuum evaporator for 8 hours. Water and acetic acid were removed during this period. Liquid chromatographic analysis of the obtained reaction product showed 96% yield of 7-amino-1-naphthyl-β-sulfatoethylsulfone.

EXAMPLES 41–47

The reaction process of Example 39 was repeated but by changing the starting material, amount of sulfuric acid added and reaction temperature as shown in the following table 3, obtaining the results also shown in the following table 3.

TABLE 3

| Example No. | Starting material | Amount of sulfuric acid (molar ratio) | Reaction temperature (°C.) | Yield (%) |
|---|---|---|---|---|
| 41 | 4-Amino-2,5-dimethoxyphenyl-β-hydroxyethylsulfone | 1.7 | 100–105 | 96 |
| 42 | 3-Amino-4-sulfophenyl-β-hydroxyethylsulfone | 2.0 | 120–125 | 92 |
| 43 | 4-Amino-1-naphthyl-β-hydroxyethylsulfone | 1.5 | 110–115 | 97 |
| 44 | 3-(4-Aminobenzoyl)aminophenyl-β-hydroxyethylsulfone | 1.05 | 85–90 | 96 |
| 45 | 3-Chloro-4-aminophenyl-β-hydroxyethylsulfone | 1.1 | 100–105 | 97 |
| 46 | 3-Carboxy-4-aminophenyl-β-hydroxyethylsulfone | 1.1 | 100–105 | 96 |
| 47 | 3-Hydroxy-4-aminophenyl-β-hydroxyethylsulfone | 1.05 | 90–95 | 97 |

EXAMPLE 48

Wet cake of 72.2 parts of 3-acetylamino-4-methoxyphenyl-β-hydroxyethylsulfone (purity: 75.6%) was added in 23.3 parts of 5% fuming sulfuric acid (1.2 times in molar quantity) under stirring and external cooling at 30°–40° C. and then the mixture was maintained at 100°–105° C. for 2 hours. This mixture was mixed well with 40 parts of diatomaceous earth and kept in a natural convection type electric constant-temperature dryer (manufactured by Mitamura Riken Kogyo Co.) at 110°–115° C. for 8 hours, and the resulting reaction product was analyzed by liquid chromatography, whereby production of 3-amino-4-methoxyphenyl-β-sulfatoethylsulfone in a yield of 97% was determined.

EXAMPLE 49

2,475 Parts of 4-acetylaminophenyl-β-hydroxyethylsulfone (purity: 98.2%) was added in 1,470 parts of 70% sulfuric acid (1.05 times in molar quantity) under stirring and maintained at 100°–105° C. for one hour. The obtained mixture was passed through a pipe reactor kept at 100° to 150° C. (the inlet temperature was 190° to 195° C.), thereby distilling off water and acetic acid. Liquid chromatographic analysis of the resulting reaction product showed 98% yield of 4-aminophenyl-β-sulfatoethylsulfone.

EXAMPLE 50

56.8 Parts of N,N'-bis[8-(β-hydroxyethylsulfonyl)-2-naphthyl] urea (purity: 93%) was added in 39.6 parts of 65% sulfuric acid (molar ratio: 1.3) under stirring and maintained at 105°–110° C. for 4 hours. Then the mixture was spray-dried by using a spray dryer with inlet temperature of 200° C. and outlet temperature of 130° C., whereby the volatile component water was removed to produce a powdery reaction product. Liquid chromatographic analysis of this reaction product gave 2-aminonaphthyl-8-(β-sulfatoethylsulfone) in a yield of 93%.

EXAMPLE 51

49.5 Parts of 4-acetylaminophenyl-β-hydroxyethylsulfone (purity: 98.2%) was added in 24.5 parts of 40% sulfuric acid (molar ratio: 0.5) under stirring and maintained at 110°–115° C. for one hour. Then water and acetic acid were distilled off under reduced pressure (400 mmHg) at 110°–115° C., and the resulting mixture was placed in an evaporating dish, added and mixed well with 15.52 parts of sulfamic acid (molar ratio: 0.8) and kept in a hot air circulation dryer (manufactured by Nishiyama Seisakujo Co.) at 120°–125° C. for 8 hours. Water and acetic acid were distilled off during this period. Liquid chromatographic analysis of the reaction product showed 96% yield of 4-aminophenyl-β-sulfatoethylsulfone and existence of small quantities of 4- aminophenyl-β-hydroxyethylsulfone and 4-aminophenyl-β-acetoxyethylsulfone in the product.

EXAMPLE 52

304.5 Parts of 3-aminophenyl-β-hydroxyethylsulfone (purity: 66%), in the form of wet cake, was fed into a two-shaft double-arm kneader (Inoue Seisakujo Co.) having a heating-cooling jacket and operated at 60/45 r.p.m. and water was distilled off under reduced pressure (600 mmHg) at 100°–105° C. The mixture was further added with 135.8 parts of sulfamic acid (molar ratio: 1.4) and maintained at 90°–95° C. for 6 hours. By-produced ammonia was removed as ammonium salt during this period. Liquid chromatographic analysis of the resulting reaction product showed 95% yield of 3-aminophenyl-β-sulfatoethylsulfone.

EXAMPLE 53

57.3 Parts of 2-methoxy-5-ureidophenyl-β-hydroxyethylsulfone (purity: 95%) was added in 22.4 parts of 70% sulfuric acid (molar ratio: 0.8) and maintained at 110°–115° C. for 2 hours. This mixture was poured into 200 parts of perchloroethylene at 115°–120° C., in which 13.58 parts of sulfamic acid (molar ratio: 0.7) had been added, for a period of 2 hours while distilling off water and then maintained at 115°–120° C. for additional one hour to complete the reaction. There was obtained 2-methoxy-5-aminophenyl-β-sulfatoethylsulfone in a yield of 93%.

EXAMPLE 54

318.5 Parts of 7-acetylamino-1-naphthyl-β-hydroxyethylsulfone (purity: 92%) was added in 310 parts of 30% sulfuric acid (molar ratio: 0.95) under stirring and maintained at 110°–115° C. for 2 hours. The mixture was cooled to 30° C., added with 38.8 parts of sulfamic acid (molar ratio: 0.4) and spray-dried by a spray dryer with inlet temperature of 200° C. and outlet temperature of 120° C. Water and acetic acid were removed and powdery 7-amino-1-naphthyl-β-sulfatoethylsulfone was obtained in a yield of 92%.

EXAMPLES 55–60

The reaction of Example 52 was repeated by changing the starting compound, kind and amount of sulfuric acid esterifying agent and reaction temperature as shown in the following table 4, obtaining the results also shown in the following table 4.

TABLE 4

| Example No. | Compound of general formula (II) | Sulfuric acid esterifying agent Kind | Molar ratio | Reaction temperature (°C.) | Yield (%) |
|---|---|---|---|---|---|
| 55 | 4-Aminophenyl-β-hydroxyethylsulfone | Sulfamic acid | 1.7 | 130–135 | 98 |
| 56 | 3-Hydroxy-4-aminophenyl-β-hydroxyethylsulfone | 5% fuming sulfuric acid, Sulfamic acid | 0.9 0.9 | 90–95 | 94 |
| 57 | 4-Amino-2,5-dimethoxyphenyl-β-hydroxyethyl sulfone | Sulfamic acid | 1.5 | 140–145 | 93 |
| 58 | 4-Amino-1-naphthyl-β-hydroxyethylsulfone | Chlorosulfonic acid | 1.1 | 60–70 | 94 |
| 59 | 3-Chloro-4-aminophenyl-β-hydroxyethylsulfone | Sulfamic acid | 1.3 | 100–105 | 96 |
| 60 | 3-Carboxy-4-aminophenyl-β-hydroxyethylsulfone | 100% sulfuric acid Sulfamic acid | 0.5 1.0 | 120–125 | 94 |

EXAMPLES 61–65

The reaction process of Example 53 was followed by changing the starting compound, kind and amount of the sulfuric acid esterifying agent, organic solvent and reaction temperature as shown in the following table 5, obtaining the results also shown in the following table 5.

TABLE 5

| Example No. | Compound of general formula (II) | Sulfuric acid esterifying agent Kind | Molar ratio | Organic solvent | Reaction temperature (°C.) | Yield (%) |
|---|---|---|---|---|---|---|
| 61 | 4-Ureidophenyl-β-hydroxyethylsulfone | 60% Sulfuric acid Sulfamic acid | 0.7 0.8 | o-dichlorobenzene | 150–160 | 97 |
| 62 | 3-Benzoylamino-4-methoxyphenyl-β-hydroxyethylsulfone | 50% sulfuric acid Sulfamic acid | 0.95 0.45 | Xylene | 120–125 | 95 |
| 63 | 4-Acetylaminophenyl-β-hydroxyethylsulfone | 40% sulfuric acid Sulfamic acid | 0.5 1.0 | Toluene | 105–110 | 98 |
| 64 | 4-Acetylamino-1-naphthyl-β-hydroxyethylsulfone | 80% sulfuric acid Sulfamic acid | 0.9 0.5 | Nitrobenzene | 170–175 | 88 |
| 65 | N,N'-bis-[4-(β-hydroxyethylsulfonyl)phenyl]urea | 70% sulfuric acid Sulfamic acid | 0.95 0.4 | Toluene | 105–110 | 97 |

REFERENTIAL EXAMPLE 1

The reaction product obtained in Example 1 was poured into icy water and, after neutralization with sodium carbonate, perchloroethylene was separated and the product without isolating was diazotized in a usual way with hydrochloric acid and sodium nitrite. This was followed by coupling with 38.9 parts of 1-amino-8-naphthol-3,6-disulfonic acid (purity: 80%) in a usual way, and the obtained reaction solution was spray-dried, whereby there was obtained a black dye known as Reactive Black 5 in Color Index, said black dye being low in inorganic salt content and high in concentration. The solution formed by adding 0.8 part of diethylene glycol monobutyl ether to the reaction solution before spray drying was a concentrated aqueous solution of dye with a low sodium sulfate content. This solution, even if left at low temperature for a long time, caused no crystal precipitation and was also excellent in storage stability.

When a cellulose fiber fabric was dyed with the obtained powdery dye or concentrated dye solution in a common way, there was obtained a fast and concentrated black dyed fabric.

REFERENTIAL EXAMPLE 2

The reaction product obtained in Example 4 was poured into icy water and, after neutralization with sodium carbonate, toluene and diatomaceous earth were removed and the product was subjected to usual diazotization with hydrochloric acid and sodium nitrite. Then the product was subjected to coupling in a usual way with 8-acetylamino-1-naphthol-3,5-disulfonic acid in a molar ratio of 1.05 and the whole product was spray-dried. There was resultantly obtained, in a high yield, a red dye same as disclosed in claim 10 of U.S. Pat. No. 3,553,189.

The solution formed by adding 0.8 part of diethylene glycol monobutyl ether without spray-drying was a concentrated aqueous solution which, even if left at low temperature, caused no precipitation of sodium sulfate and was also excellent in storage stability.

When cellulose fibers were dyed in a usual way by using these dye products, where were obtained the fast and concentrated red dyed fabrics.

REFERENTIAL EXAMPLE 3

The reaction mixture obtained in Example 19 was put into icy water and, without isolating the product, diazotized in a normal way with hydrochloric acid and sodium nitrite, following by coupling and drying in the same way as Referential Example 1. There was obtained a black dye known as Reactive Black 5 in Color Index, said black dye being low in inorganic salt content and high in concentration.

REFERENTIAL EXAMPLE 4

The reaction product obtained in Example 22 was put into icy water and, after neutralization with sodium carbonate and successive removal of xylene and diatomaceous earth, the product was diazotized in a known way with hydrochloric acid and sodium nitrite. This was followed by coupling in a usual way with 1.1 time the molar quantity of 3-sulfo-7-acetylamino-naphthol and the whole product was spray-dried, whereby there was obtained an orange dye known as C.I. Reactive Orange 16 in a high yield. The solution formed by adding 4.0 parts of diethylene glycol monobutyl ether to the reaction solution before spray-drying was a concentrated aqueous solution which was low in sodium sulfate content, caused no crystal precipitation even if left at low temperature and had excellent storage stability.

When cellulose fibers were dyed in a common way by using these dye products, there were obtained the fast and concentrated reddish orange dyed fabrics.

REFERENTIAL EXAMPLE 5

The reaction mixture obtained in Example 35 was put into icy water and, without isolating the product, subjected to usual diazotization with hydrochloric acid and sodium nitrite, followed by the same treatment as in Referential Example 1 to obtain a black dye known as C.I. Reactive Black 5, said black dye having high concentration and low inorganic salt content.

REFERENTIAL EXAMPLE 6

The reaction product obtained in Example 36 was put into icy water and, after neutralization with sodium carbonate and successive removal of diatomaceous earth, the product was subjected to usual diazotization with hydrochloric acid and sodium nitrite, followed by the same treatment as in Referential Example 2. There was obtained, in a high yield, a red dye same as disclosed in claim 10 of U.S. Pat. No. 3,553,189.

REFERENTIAL EXAMPLE 7

The reaction product obtained in Example 49 was put into icy water and diazotized in a usual way with hydrochloric acid and sodium nitrite. This was followed by coupling in a known way with 1.05 times the molar quantity of 3-sulfo-7-acetylamino-1-naphthol and the whole product without isolating, was subjected to spray drying. There was obtained, in a high yield, a reddish orange dye known as C.I. Reactive Orange 16.

REFERENTIAL EXAMPLE 8

The reaction mixture obtained in Example 51 was put into icy water and, without isolating the product, subjected to usual diazotization with hydrochloric acid and sodium nitrite, followed by coupling in a known way with 38.9 parts of 1-amino-8-naphthol-3,6-disulfonic acid (purity: 80%). By spray drying this reaction solution, there was obtained a black dye known as Reactive Black 5 in Color Index, said black dye being a high-concentration product with low inorganic salt content.

REFERENTIAL EXAMPLE 9

The reaction product obtained in Example 53 was put into icy water and after neutralization with sodium carbonate and successive separation of perchloroethylene, the product was subjected to usual diazotization with hydrochloric acid and sodium nitrite, followed by the same treatment as in Referential Example 2. There was obtained, in a high yield, a red dye same as disclosed in claim 10 of U.S. Pat. No. 3,553,189.

What is claimed is:

1. A process for producing a sulfuric acid semiester of the formula (I):

$$NH_2-A-(SO_2CH_2CH_2OSO_3H)_n \qquad (I)$$

wherein A is phenylene, naphthylene,

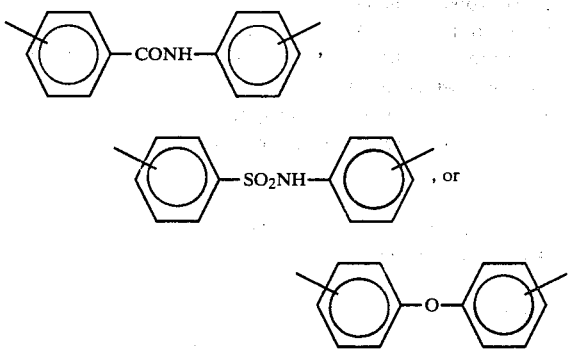

which may be substituted with one or two methyl, methoxy, hydroxy, chloro, carboxylic or sulfonic acid groups and n is an integer of 1 or 2, which comprises subjecting a mixture of an acid and a compound of the formula (II-1) or (II-2):

$$NH_2\text{—}A\text{—}(SO_2CH_2CH_2OH)_n \qquad \text{(II-1)}$$

$$B\text{—}NH\text{—}A\text{—}(SO_2CH_2CH_2OH)_n \qquad \text{(II-2)}$$

wherein A and n are as defined above and B is a group capable of being hydrolyzed by an acid, to reaction, while removing a volatile matter from the reaction system, in a reaction zone capable of removing the volatile matter by azeotropy with an organic solvent, evaporation or vaporization, whereby esterification of said compound of the formula (II-1) or hydrolysis and esterification of said compound of the formula (II-2) is effected, the acid in the reaction system being sulfuric acid and the amount of the acid being 1 to 2 moles per mole of β-hydroxyethylsulfonyl group in the compound of the formula (II-1) or (II-2).

2. The process according to claim 1, wherein the reaction is carried out at a temperature of 40° to 250° C.

3. The process according claim 1, wherein the compound of the formula (II-2) is $CO(NH\text{—}A\text{—}SO_2CH_2CH_2OH)_2$.

4. The process according to claim 1, wherein the initial concentration in the reaction system of sulfuric acid is from 20 to 100% by weight.

5. The process according to claim 1, wherein the reaction is carried out in the presence of diatomaceous earth, activated clay, active carbon, silica gel, brown coal or aminoaryl-β-sulfatoethylsulfone corresponding to the reaction product.

6. The process according to claim 1, wherein the reaction is carried out in the presence of an inert gas or under reduced pressure.

* * * * *